United States Patent [19]

Albrecht et al.

[11] Patent Number: 4,610,818

[45] Date of Patent: Sep. 9, 1986

[54] N-ACYL DERIVATIVES OF DIPEPTIDES, THEIR PREPARATION AND THEIR USE IN THE THERAPY OF DISORDERS, AND AGENTS FOR THIS PURPOSE

[75] Inventors: Hans P. Albrecht, Weinheim; Horst Kreiskott, Wachenheim, both of Fed. Rep. of Germany

[73] Assignee: BASF Aktiengesellschaft, Ludwigshafen, Fed. Rep. of Germany

[21] Appl. No.: 513,052

[22] Filed: Jul. 12, 1983

[30] Foreign Application Priority Data

Jul. 14, 1982 [DE] Fed. Rep. of Germany ....... 3226242

[51] Int. Cl.[4] .......................... A61K 37/02; C07K 5/02
[52] U.S. Cl. ...................................... 514/19; 260/998.2
[58] Field of Search .................... 260/112.5; 424/177; 514/2

[56]  References Cited

U.S. PATENT DOCUMENTS 3,778,428 12/1973 Mukaiyama ...................... 260/112.5
4,018,912 4/1977 Failli et al. .......................... 424/177

OTHER PUBLICATIONS

Englehardt et al, "Antiparkinsonism Drugs" in *Medicinal Chemistry*, 3rd Ed., Part II, 1970, pp. 1538–1543.
Collection of Czechoslovak Chemical Communications 45, 294–297.
Chemical Abstracts 95, 767 (1981) No. 62675u.
Journal of Medicinal Chemistry 22, 931–933 (1979).
Chemical Abstracts 55, 20034d (1961).
Chemical Abstracts 95, 766 (1981) No. 62644a.

*Primary Examiner*—Donald B. Moyer
*Assistant Examiner*—Jacqueline M. Stone
*Attorney, Agent, or Firm*—Keil & Weinkauf

[57]  ABSTRACT

N-acyl derivatives of dipeptides of the formula

X-CO-L-Leu-NH-CH$_2$-CO-R where X and R have the meanings given in the description, are useful for the therapy of disorders.

6 Claims, No Drawings

N-ACYL DERIVATIVES OF DIPEPTIDES, THEIR PREPARATION AND THEIR USE IN THE THERAPY OF DISORDERS, AND AGENTS FOR THIS PURPOSE

The present invention relates to novel N-acyl derivatives of dipeptides, processes for their preparation, drugs which contain these novel compounds and their use for the therapy of disorders.

The tripeptide L-Pro-L-Leu-Gly-$NH_2$ (MIF) is the melanocyte stimulating hormone-release inhibiting factor (The Merck Index, 9th Edition, 1976). In addition to its endocrinal action, the tripeptide has a neurotransmitter or neuromodulator effect in the central nervous system. Clinical studies have shown that MIF alone or in combination with L-dopa has an advantageous effect on tremor, rigor and akinesia in Parkinson patients (A. J. Kastin and A. Barbeau, Can. Med. Assoc. J. 107, (1972), 1097 and F. Gerstenbrand et al., Wien. klin. Wschr. 87, (1975), 822).

However, wide therapeutic use of this tripeptide is hindered by the lack of sufficient oral activity and the short duration of action.

Attempts have also been made to prepare, by means of molecular transformation in which the pharmacological activity of L-Pro-L-Leu-Gly-$NH_2$ is retained, compounds which have oral activity and an adequate duration of action.

Efforts have been concentrated on exchanging the central L-leucine for D-leucine (U.S. Pat. No. 4,278,595) or for an N-alkyl derivative of L- or D-Leucine (German Laid-Open Application DOS 2,633,976).

The replacement of the L-proline by an acid or amino acid has been little investigated to date, since, apart from exchange for L-pyroglutamic acid, which does not have an adverse effect (S. Bjorkman et al., Acta. Pharm. Suec. 13, (1976) 289), the products obtained are pharmacologically inactive (R. C. Johnson et al., J. Med. Chem. 21, (1978) 165).

We have found that N-acyl derivatives of dipeptides of the formula I

X-CO-L-Leu-NH-$CH_2$-CO-R    I where X is a saturated cycloaliphatic hydrocarbon radical of 3 to 10 carbon atoms, indanyl or 1,2,3,4-tetrahydronaphthyl, in which radicals the carbon atom which is bonded to the carbonyl group can also carry an amino group, or X is a saturated or unsaturated 4-membered, 5-membered or 6-membered heterocyclic ring system containing not more than 2 heteroatoms, and the heterocyclic structure may furthermore be fused to a benzene nucleus and, where the heterocyclic structure contains nitrogen, it may also contain an oxo or a $C_1$–$C_3$-alkyl group, and R is $C_1$–$C_5$-alkoxy or a radical $NR^1R^2$, where $R^1$ and $R^2$ are identical or different and are each hydrogen or $C_1$–$C_5$-alkyl, but where X (a) cannot be pyrrolidin-2-yl or 5-oxopyrrolidin-2-yl,
(b) cannot be cyclopentyl if R is amino or ethylamino, and
(c) cannot be 4-thiazolidinyl if R is amino, and their salts with physiologically tolerated acids are good therapeutics, either alone or in combination with L-dopa.

In formula I, X is preferably a saturated cycloaliphatic hydrocarbon radical of 5 to 7 carbon atoms, indanyl or 1,2,3,4-tetrahydronaphthyl, in which radicals the carbon atom which is bonded to the carbonyl group also carries an amino group. Other preferred compounds are those in which X is a saturated or unsaturated ring system of 4 or 5 carbon atoms and one nitrogen atom, where one carbon atom can be replaced by a sulfur atom or a further nitrogen atom, and the heterocyclic structure is fused to a benzene nucleus and may or may not carry an oxo group at a carbon atom adjacent to the nitrogen atom. In these compounds, the radical -CO-L-Leu-NH-$CH_2$-CO-R is located at a carbon atom adjacent to the nitrogen atom.

Particularly preferred compounds are those in which X has one of the above meanings and R is $NR^1R^2$.

Particularly suitable physiologically tolerated acids are hydrochloric acid, sulfuric acid, phosphoric acid, acetic acid, lactic acid, succinic acid, fumaric acid and malic acid.

The novel N-acyl dipeptides of the formula I can be prepared by methods generally used in peptide chemistry. The various reactions are carried out after the amine function has been blocked by means of suitable protective groups which do not interfere in the reaction. Splitting off the protective groups after the reaction is complete is also carried out by a method conventionally used in peptide chemistry (cf. E. Wünsch in Methoden der Organischen Chemie, Volumes XV/1 and XV/2, edited by E. Müller, Georg Thieme Verlag, Stuttgart 1974).

In particular, the novel compounds are prepared by a method wherein (a) where X does not contain a basic amino group, a carboxylic acid of the formula II

X-COOH    II is allowed to act on a dipeptide of the formula III

L-Leu-NH-$CH_2$-CO-R    III where R has the above meanings, or (b) where X contains a basic amino group, the compound of the formula II, whose amino group carries a protective group, is condensed with a dipeptide of the formula III, and the protective group is then split off, and, if desired, the resulting compound is converted to its salts with physiologically tolerated substances.

Carboxylic acids of the general formula I, or their activated derivatives, which possess an asymmetrically substituted carbon atom, can be employed either in the form of their optically pure isomers or in the form of their racemates. In the latter case, condensation with the optically active dipeptide of the formula II gives a diastereomer mixture, which can be separated by chromatography or crystallization.

For the reaction (a) it is generally necessary to activate the free acid function of the carboxylic acid of the formula II before it acts on the dipeptide of the formula III. Activated derivatives of the carboxylic acid are preferably the mixed anhydrides, which are prepared in situ in the presence of an alkyl chloroformate, e.g. isobutyl chloroformate or ethyl chloroformate, as well as adducts of carbodiimides, preferably dicyclohexylcarbodiimide, or activated esters, preferably the N-hydroxysuccinimide esters which, if appropriate, can be prepared in situ from N-hydroxysuccinimide and dicyclohexylcarbodiimide. The condensation of the activated derivative is carried out in an organic solvent, e.g. dioxane, tetrahydrofuran, dichloromethane, chloroform, toluene or dimethylformamide, or in an aqueous organic medium in the presence of a base. Preferred bases are triethylamine, N-methylmorpholine and sodium bicarbonate. The reaction temperature is from −10° to +30° C. and the reaction time is from 3 hours to 4 days.

For process (b), the protective groups for the amino group are those conventionally used in peptide chemistry, preferably benzyloxycarbonyl, t-butoxycarbonyl or benzhydryl.

It is generally necessary to activate the free acid function of the carboxylic acid before it acts on the dipeptide of the formula III. Activated derivatives of the carboxylic acid are preferably the mixed anhydrides, which are prepared in situ in the presence of an alkyl chloroformate, e.g. isobutyl chloroformate or ethyl chloroformate, as well as adducts of carbodiimides, preferably dicyclohexylcarbodiimide, or activated esters, preferably the N-hydroxysuccinimide esters which, if appropriate, can be prepared in situ from N-hydroxysuccinimide and dicyclohexylcarbodiimide.

The condensation of the activated derivative is carried out in an organic solvent, e.g. dioxane, tetrahydrofuran, dichloromethane, chloroform, toluene or dimethylformamide, or in an aqueous organic medium in the presence of a base. Preferred bases are triethylamine, N-methylmorpholine and sodium bicarbonate. The reaction temperature is from −10° to +30° C. and the reaction time is from 3 hours to 4 days.

The condensation reaction gives protected derivatives of the compounds of the formula I. These are converted to the novel compounds of the formula I by splitting off the protective group. Where the protective group is benzyloxycarbonyl or benzhydryl, these are advantageously split off by hydrogenation in the presence of a noble metal catalyst in an inert solvent at room temperature. Preferred noble metal catalysts are palladium, platinum or Raney nickel. In a preferred embodiment, 10% strength palladium on carbon is used. Preferred solvents are methanol, ethyl acetate and glacial acetic acid. Where the protective group is t-butoxycarbonyl, this is advantageously split off by treating the intermediate with an excess of trifluoroacetic acid or with a solution of hydrogen chloride in an inert organic solvent, e.g. ethyl acetate, dioxane or tetrahydrofuran. The cleavage reaction is carried out at from 0° to 20° C. for from 5 to 30 minutes.

The novel N-acyl derivatives of dipeptides are substantially stable to the action of proteolytic enzymes, are active after oral administration, and have a long duration of action.

The superiority of the novel substances is shown, in particular, in the following test models:

1. In accordance with G. M. Everett (in Antidepressant Drugs, edited by S. Garattini and M. N. G. Dukes, Amsterdam 1967, pages 164 et seq.), an L-dopa/pargyline combination which causes a weak pattern of excitation is administered to mice. A pronounced pattern of excitation develops only as a result of pretreatment with substances which stimulate the central nervous system. In this test model, the novel tripeptides are effective when administered orally in doses of 0.02 mg/kg and more.

2. In addition to peripheral symptoms, centrally induced scratching results when the cholinomimetic pilocarpine is administered to rats (H. Kreiskott, Arch. exp. Path. Pharmak. 247 (1964), 317); this scratching can be prevented by means of central anticholinergics or central monaminergic stimulants (H. Kreiskott and H. P. Hofmann, 6th Int. Congress Pharmacol., Helsinki 1975, Abstr. 825). Oral pretreatment with the novel tripeptides suppresses the centrally induced scratching due to pilocarpine.

3. The action pattern and toxicity pattern of the substances effective in test models 1 and 2 were additionally tested on the mouse. The symptoms were detected and quantified by the method due to S. Irwin (Psychopharmakologia 13 (1968), 222). The various test parameters are measured shortly before administration of the substance as well as ½, 1, 2, 3 and 24 hours after oral administration. Each dose was administered to a group of 3 animals, and the first test of behavior was carried out after allowing the animals 30 minutes to become accustomed to the macrolon cage. Basic behavior, central stimulation and depression as well as autonomic symptoms are measured. In particular, these are:

posture
position of limbs
cleaning behavior
stupor
spontaneous and induced locomotor activity
respiration
sensomotor reactions (reflexes)
width of palpebral fissure
pupil size and
body temperature, etc.

The novel substances produce higher locomotor activity as well as increased sniffing, standing up and cleaning. These symptoms occur to an equal extent both in the case of dopaminergic substances and in the case of dopamine-stimulating substances.

Accordingly, the novel substances clearly stimulate dopaminergic processes. In test model 1 (L-dopa potentiation), the action of exogenic dopamine is increased, while in 2 (pilocarpine stimulation) and 3 (action pattern) the effect of the endogenic dopamine is reinforced.

4. Rats pretreated subcutaneously with average doses of morphine do not show any striking features in their overall behavior. However, if an additional external stimulus, such as placing a clip on the tail, is applied, the animals abruptly become rigid and exhibit catalepsy. When the stimulus is removed, the rats again behave normally (G. Stille, Zur Pharmakologie katatonigener Stoffe, Aulendorf 1971, page 30). This stimulus-induced condition can be prevented by means of an intravenous injection of the claimed tripeptides.

The novel peptides, either alone or in combination with L-dopa, are therefore useful for the oral therapy of depressions. They can also be employed for preventing or treating opiate dependence.

The novel compounds can be administered in a conventional manner, either orally or parenterally (subcutaneously, intravenously, intramuscularly or intraperitoneally). They may also be administered through the nasopharyngeal space by means of vapors or sprays.

The dose depends on the age, condition and weight of the patient and on the route of administration. As a rule, the daily dose of active compound is from about 0.1 to 100 mg/kg of body weight when administered orally, and from about 0.01 to 10 mg/kg of body weight when administered parenterally.

The novel compounds can be used in the conventional solid or liquid pharmaceutical forms, for example tablets, film tablets, capsules, powders, granules, coated tablets, suppositories, solutions or sprays. These are prepared in a conventional manner, and to do so the active compounds can be mixed with the conventional pharmaceutical auxiliaries, such as tablet binders, fillers, preservatives, tablet disintegrators, flow regulators, softeners, wetting agents, dispersants, emulsifiers, solvents, retarding agents, antioxidants and/or propellants (cf. H. Sucker et al, Pharmazeutische Technologie, Thieme-Verlag, Stuttgart, 1978). The resulting forms for administration usually contain the active compound in an amount of from 0.1 to 99% by weight.

EXPERIMENTAL SECTION

The Examples which follow illustrate the invention without restricting it.

All the reactions were monitored by means of thin-layer chromatography on $F_{254}$ precoated silica gel plates from Merck. Depending on the polarity of the compounds investigated, the mobile phase used was dichloromethane/acetone (from 20:1 to 5:1), dichloromethane/methanol (from 20:1 to 2:1) or butanol-/ethyl acetate/glacial acetic acid/water (4:1:1:1).

The novel compounds of the general formula I obtained in the Examples below are pure according to thin-layer chromatography.

The NMR spectra are in agreement with the structure given.

Celit ® is a filtration assistant from Johns-Manville.

EXAMPLE 1

Pyrrol-2-yl-carbonyl-L-leucyl-glycinamide 7.0 ml of triethylamine and 10.4 g of the N-hydroxysuccinimide ester of pyrrole-2-carboxylic acid were added to 9.4 g of L-leucyl-glycinamide in 120 ml of dioxane at 10° C. and the reaction mixture was stirred for 2 hours at this temperature, after which 30 ml of water were added and the stirred mixture was allowed to react for 20 hours at room temperature.

In the working up procedure, the mixture was taken up in ethyl acetate and the organic phase was washed successively with 10% strength aqueous citric acid solution, sodium carbonate solution and water, dried over sodium sulfate and evaporated down under reduced pressure. Chromatography of the residue over a silica gel column (elution with 10:1 dichloromethane/methanol) gave 5.0 g (36%) of pyrrol-2-yl-carbonyl-L-Leycyl-glycinamide, $[\alpha]_D^{20} = -2°$ (c =0.5, methanol).

The compounds below were obtained by methods similar to that described in Example 1:

2. Thiophen-2-yl-carbonyl-L-leucyl-glycinamide (56%), mp.=155°-165° C. (dichloromethane/ether/petroleum ether), $[\alpha]_D^{20} = -11°$ (c =0.5, methanol);
3. furan-2-yl-carbonyl-L-leucyl-glycinamide (44%), $[\alpha]_D^{20} = +5°$ (c =0.5, methanol);
4. thiophen-3-yl-carbonyl-L-leucyl-glycinamide (46%), $[\alpha]_D^{20} = -3°$ (c =0.3, methanol);
5. D,L-tetrahydrofuran-2-yl-carbonyl-L-leucyl-glycinamide (56%), mp. =109°-122° C. (dichloromethane/hexane), $[\alpha]_D^{20} = -8°$ (c =0.5, methanol);
6. D,L-tetrahydrothiophen-2-yl-carbonyl-L-leucyl-glycinamide (32%), mp. =149°-151° C. (dichloromethane/ether), $[\alpha]_D^{20} = -12°$ (c =0.5, methanol);
7. cyclobutylcarbonyl-L-leucyl-glycinamide (41%), mp. =126°-136° C. (dichloromethane/ether), $[\alpha]_D^{20} = -20°$ (c =0.5, methanol);
8. cyclohexylcarbonyl-L-leucyl-glycinamide (54%), mp. =196°-197° C. (dichloromethane/methanol/ether);
9. indol-2-yl-carbonyl-L-leucyl-glycinamide (58%), mp. =203°-204° C. (dichloromethane/methanol/ether), $[\alpha]_D^{20} = 8°$ (c =0.5, methanol);
10. benzoyl-L-leucyl-glycinamide (55%), mp. =147°-150° C. (dichloromethane/ether);
11. pyrid-3-yl-carbonyl-L-leucyl-glycinamide (38%), $[\alpha]_D^{20} = +4°$ (c =0.5, methanol);
12. indol-2-yl-carbonyl-L-leucyl-glycine ethyl ester (63%), $[\alpha]_D^{20} = -9°$ (c =0.5, methanol);
13. pyrrol-2-yl-carbonyl-L-leucyl-glycine ethyl ester (55%), mp. =169°-170° C. (methanol/ether), $[\alpha]_D^{20} = -25°$(c =0.5, methanol);
14. L-piperid-2-on-6-yl-carbonyl-L-leucyl-glycinamide (31%), mp. =98°-108° C., $[\alpha]_D^{20} = -4°$ (c =0.5, methanol).

EXAMPLE 15

Adamant-1-yl-carbonyl-L-leucyl-glycinamide 2.0 ml of isobutyl chloroformate were added dropwise to 2.7 g of adamantane-1-carboxylic acid and 2.0 ml of triethylamine in 40 ml of dimethylformamide at −10° C., while stirring, 2.8 g of L-leucyl-glycinamide were added to the resulting solution of the asymmetric acid anhydride after 15 minutes and the mixture was stirred for 1 hour at −10° C. and then for 16 hours at room temperature, after which it was evaporated down under reduced pressure.

In the working up procedure, the mixture was taken up in ethyl acetate, and the solution was washed successively with 10% strength aqueous citric acid solution, sodium carbonate solution and water, dried over sodium sulfate and evaporated down under reduced pressure. Chromatography of the residue over a silica gel column (elution with 10:1 dichloromethane/methanol) gave 2.7 g (52%) of adamant-1-yl-carbonyl-L-leucyl-glycinamide of melting point 123°-127° C. (dichloromethane/ether/hexane).

The following compound was obtained by a method similar to that described in Example 15:

16. pyrid-2-yl-carbonyl-L-leucyl-glycinamide (52%), mp. =141°-146° C. (dichloromethane/hexane), $[\alpha]_D^{20} = +7°$ (c =0.5, methanol).

EXAMPLE 17

D-1,2,3,4-Tetrahydroquinol-2-yl-carbonyl-L-leucyl-glycinamide and

L-1,2,3,4-tetrahydroquinol-2-yl-carbonyl-L-leucyl-glycinamide 8.4 ml of triethylamine and 12.3 g of the N-hydroxysuccinimide ester of 1,2,3,4-tetrahydroquinoline-2-carboxylic acid were added to 5.6 g of L-leucyl-glycinamide in 60 ml of dioxane at 10° C. and the reaction mixture was stirred for 3 hours at this temperature, after which 30 ml of water were added and the mixture was allowed to react for 20 hours at room temperature. It was taken up in ethyl acetate, and the organic phase was washed successively with 10% strength aqueous citric acid solution, sodium carbonate solution and water, dried over sodium sulfate and evaporated down under reduced pressure. Chromatography over a silica gel column (elution with 20:1 dichloromethane/methanol) gave the two isomers in pure form:

benzyloxycarbonyl-D-1,2,3,4-tetrahydroquinol-2-yl-carbonyl-L-leucyl-glycinamide, yield 3.8 g (26%), mp. =163°-173° C. (isopropanol/ether), $[\alpha]_D^{20} = +23°$ (c =0.5, methanol);

benzyloxycarbonyl-L-1,2,3,4-tetrahydroquinol-2-yl-carbonyl-L-leucyl-glycinamide, yield 2.9 g (20%), mp. =142°–145° C. (isopropanol/diisopropyl ether), $[\alpha]_D^{20} = -88°$ (c =0.5, methanol).

2.1 g of benzyloxycarbonyl-D-1,2,3,4-tetrahydroquinol-2-yl-carbonyl-L-leucyl-glycinamide were dissolved in 150 ml of methanol and hydrogenated in the presence of 0.2 g of palladium on carbon (10%). After the theoretical amount of hydrogen had been absorbed, the mixture was filtered over Celit, the filtrate was evaporated down under reduced pressure and the residue was crystallized from ethyl acetate/ether/hexane. 1.0 g (66%) of D-1,2,3,4-tetrahydroquinol-2-yl-carbonyl-L-leucyl-glycinamide were obtained; mp. =137°–140° C., $[\alpha]_D^{20} = +36°$ (c =0.5, methanol).

Benzyloxycarbonyl-L-1,2,3,4-tetrahydroquinol-2-yl-carbonyl-L-leucyl-glycinamide was converted, by a similar method, to 1.5 g (70%) of L-1,2,3,4-tetrahydroquinol-2-yl-carbonyl-L-leucyl-glycinamide; mp. =73°–85° (ethyl acetate/ether/petroleum ether), $[\alpha]_D^{20} = -50°$ (c =0.5, methanol).

EXAMPLE 18

The procedure described in Example 17 was followed, except that the chromatographic separation of the two isomers over a silica gel column (elution with 10:1 dichloroethane/methanol) was carried out only at the stage of the end product. The following compounds were obtained in order of increased polarity:

(18a) L-1,2,3,4-tetrahydroisoquinol-3-yl-carbonyl-L-leucyl-glycinamide; yield 40% of theory, mp. =160°–163° C., $[\alpha]_D^{20} = -69°$ (c =0.5, methanol) and (18b) D-1,2,3,4-tetrahydroisoquinol-3-yl-carbonyl-L-leucyl-glycinamide; yield 20% of theory, mp. =176°–181° C., $[\alpha]_D^{20} = +42°$ (c =0.5, methanol).

EXAMPLE 19

4,5-Dehydropiperid-2-yl-carbonyl-L-leucyl-glycinamide 6.0 ml of isobutyl chloroformate were added dropwise to 9.1 g of N-tert.-butoxycarbonyl-4,5-dehydropiperidine-2-carboxylic acid and 6.1 ml of triethylamine in 100 ml of absolute tetrahydrofuran at −10° C., while stirring, 2.2 g of L-leucyl-glycinamide in 100 ml of a 1:2 dimethylformamide/tetrahydrofuran mixture were added to the resulting solution of the asymmetric acid anhydride after 15 minutes and the mixture was stirred for 1 hour at −10° C. and then for 16 hours at room temperature, after which it was evaporated down under reduced pressure. In the working up procedure, the mixture was taken up in ethyl acetate and the solution was washed successively with 10% strength aqueous citric acid solution, sodium carbonate solution and water, dried over sodium sulfate and evaporated down under reduced pressure. Purification over silica gel (elution with 10:1 dichloromethane/methanol) gave 9.0 g (57%) of N-tert.-butoxycarbonyl-4,5-dehydropiperid-2-yl-carbonyl-L-leucyl-glycinamide.

This was treated with 100 ml of an about 6 N solution of hydrogen chloride in dioxane for 15 minutes at room temperature, the mixture was evaporated down under reduced pressure and the residue was then repeatedly evaporated together with toluene and crystallized from methanol/ether.

Yield: 5.6 g (74%) of 4,5-dehydropiperid-2-yl-carbonyl-L-leucyl-glycinamide hydrochloride, mp. =213°–215° C. (methanol/ether), $[\alpha]_D^{20} = -23°$ (c =0.5, methanol).

EXAMPLE 20

L-Homoprolyl-L-leucyl-glycinamide 6.3 ml of triethylamine and 11.5 g of the N-hydroxysuccinimide ester of N-benzyloxycarbonyl-L-homoproline were added to 4.2 g of L-leucyl-glycinamide in 30 ml of dioxane at 10° C. and the reaction mixture was stirred for 2 hours at this temperature, after which 5 ml of water were added and the mixture was allowed to react for 20 hours at room temperature. In the working up procedure, the mixture was taken up in ethyl acetate and the solution was washed successively with 10% strength aqueous citric acid solution, sodium carbonate solution and water, dried over sodium sulfate and evaporated down under reduced pressure. The residue was purified by chromatography over a silica gel column (elution with 15:1 dichloromethane/methanol) to give 1.8 g of N-benzyloxycarbonyl-L-homoprolyl-L-leucyl-glycinamide. This was dissolved in 100 ml of methanol and hydrogenated in the presence of 0.3 g of palladium on carbon (10%). The mixture was filtered over Celit ® and the filtrate was evaporated down under reduced pressure. Yield: 0.8 g (90%) of L-homoprolyl-L-leucyl-glycinamide, $[\alpha]_D^{20} = -13.6°$ (c =0.5, methanol).

The compounds below were obtained by a procedure similar to that described in Example 20:

21. D,L-piperid-2-yl-carbonyl-L-leucyl-glycinamide (35%), mp. =75°–80° C. (ethyl acetate/ether), $[\alpha]_D^{20} = -16°$ (c=0.5, methanol).

22. Anthranyl-L-leucyl-glycinamide (55%), mp. =64°–69° C., $[\alpha]_D^{20} = -37°$ (c =0.5, methanol).

23. L-3-Methylprolyl-L-leucyl-glycinamide (43%), mp. =110°–116° C. (methanol/isopropyl ether).

EXAMPLE 24

L-Azetidin-2-yl-carbonyl-L-leucyl-glycinamide and D-azetidin-2-yl-carbonyl-L-leucyl-glycinamide 2.6 ml of triethylamine and 3.6 g of the N-hydroxysuccinimide ester of benzhydrylazetidine-2-carboxylic acid were added to 1.9 g of L-leucyl-glycinamide in 10 ml of dioxane at 10° C. and, after 2 hours at this temperature, 5 ml of water were added and the reaction mixture was stirred for 20 hours at room temperature. In the working up procedure, the mixture was taken up in ethyl acetate and the solution was washed successively with 10% strength aqueous citric acid solution, sodium carbonate solution and water, dried over sodium sulfate and evaporated down under reduced pressure. Chromatography over a silica gel column (elution with 15:1 dichloromethane/methanol) gave, in order of increasing polarity, the following two isomers in pure form:

1.3 g (30%) of benzhydryl-L-azetidin-2-yl-carbon-yl-L-leucyl-glycinamide, mp. =88°–90° C;

1.7 g (39%) of benzhydryl-D-azetidin-2-yl-carbon-yl-L-leucyl-glycinamide, mp. =90°–95° C.

1.3 g of benzhydryl-L-azetidin-2-yl-carbonyl-L-leucyl-glycinamide were dissolved in methanol and hydrogenated in the presence of 0.3 g of palladium on carbon (10%). The mixture was filtered over Celit ® and then evaporated down under reduced pressure to give 0.75 g (94%) of L-azetidin-2-yl-carbonyl-L-leucyl-glycinamide, $[\alpha]_D^{20} = -75°$ (c =0.5, methanol).

Benzhydryl-D-azetidin-2-yl-carbonyl-L-leucyl-glycinamide was converted, by a similar method, to 1.5 g (90%) of D-azetidin-2-yl-carbonyl-L-leucyl-glycinamide, mp. =110°–120° C., $[\alpha]_D^{20} = +16°$ (c =0.5, methanol).

EXAMPLE 25

D-2-Methylprolyl-L-leucyl-glycinamide and L-2-methylprolyl-L-leucyl-glycinamide 7 ml of isobutyl chloroformate were added dropwise to 13.0 g of benzyloxycarbonyl-D,L-2-methylproline and 7 ml of triethylamine in 100 ml of tetrahydrofuran at −10° C., while stirring, 9.5 g of L-leucyl-glycinamide in 50 ml of dimethylformamide were added to the resulting solution of the asymmetric acid anhydride after 15 minutes and, after 1 hour at −10° C., the mixture was stirred for a further 24 hours at room temperature. In the working up procedure, the mixture was taken up in ethyl acetate and the solution was washed successively with 10% strength citric acid solution, sodium carbonate solution and water and then evaporated down under reduced pressure. Chromatography of the residue over a silica gel column (elution with 15:1 toluene/methanol) gave, in order of increasing polarity, the two isomers in pure form:

3.7 g (17%) of benzyloxycarbonyl-D-2-methylprolyl-L-leucyl-glycinamide and 33 g (15%) of benzyloxycarbonyl-L-2-methylprolyl-L-leucyl-glycinamide.

0.9 g of benzyloxycarbonyl-D-2-methylprolyl-L-leucyl-glycinamide were hydrogenated in methanol in the presence of 0.2 g of palladium on carbon (10%). The mixture was filtered over Celit ® and then evaporated down under reduced pressure to give 0.6 g (97%) of D-2-methyl- prolyl-L-leucyl-glycinamide, $[\alpha]_D^{20} = -38°$ (c =0.5, methanol).

Benzyloxycarbonyl-L-2-methylprolyl-L-leucyl-glycinamide was converted, by a similar method, to L-2-methylprolyl-L-leucyl-glycinamide, $[\alpha]_D^{20} = +11°$ (c =0.5, methanol).

The following compounds were obtained by a similar procedure:

26a. D-1-amino-indan-1-yl-carbonyl-L-leucyl-glycinamide (21%), $[\alpha]_D^{20} = -4°$ (c =0.5, methanol);

26b. L-1-amino-indan-1-yl-carbonyl-L-leucyl-glycinamide (18%), mp. =82°–87° C. (ethyl acetate/petroleum ether), $[\alpha]_D^{20} = -27°$ (c =0.5, methanol).

EXAMPLE 27

1-Aminocyclohex-1-yl-carbonyl-L-leucyl-glycinamide 4 ml of isobutyl chloroformate were added dropwise to 7.9 g of 1-benzyloxycarbonylaminocyclohexane-1-carboxylic acid and 4 ml of triethylamine in 75 ml of tetrahydrofuran at −10° C., while stirring, 5.6 g of L-leucyl-glycinamide in 50 ml of dimethylformamide were added to the resulting solution of the asymmetric acid anhydride after 15 minutes, and the mixture was stirred for 1 hour at −10° C. and then for 16 hours at room temperature, after which it was evaporated down under reduced pressure. The residue was taken up in ethyl acetate and the solution was washed successively with 10% strength aqueous citric acid solution, sodium carbonate solution and water, dried over sodium sulfate and evaporated down under reduced pressure. 7.5 g of 1-benzyloxycarbonylaminocyclohex-1-yl-carbonyl-L-leucyl-glycinamide were obtained.

5.7 g of this compound were taken up in methanol and hydrogenated over palladium on carbon (10%) to give 3.6 g (93%) of 1-aminocyclohex-1-yl-carbonyl-L-leucylglycinamide of melting point 136°–147° C. (isopropanol/ether/hexane).

The compounds below were obtained by a method similar to that described in Example 27:

28. 1-aminocyclohept-1-yl-carbonyl-L-leucyl-glycinamide (49%), mp. =65°–70° C. (acetone/ether/hexane), $[\alpha]_D^{20} = -8°$ (c =0.8, methanol);

29. 2-amino-indan-2-yl-carbonyl-L-leucyl-glycinamide (61%), mp. =72°–80° C. (ethyl acetate/pentane), $[\alpha]_D^{20} = -4°$ (c =0.5, methanol).

EXAMPLE 30

1-Aminocycloprop-1-yl-carbonyl-L-leucyl-glycinamide 1.7 ml of triethylamine and 3.6 g of the N-hydroxysuccinimide ester of 1-butoxycarbonylaminocyclopropane-1-carboxylic acid were added to 2.3 g of L-leucyl-glycinamide in 30 ml of dioxane at 10° C., the reaction mixture was stirred for 1 hour at this temperature, 10 ml of water were added and the reaction was continued for 20 hours at room temperature. In the working up procedure, the mixture was taken up in ethyl acetate and the solution was washed successively with 10% strength aqueous citric acid solution, sodium carbonate solution and water, dried over sodium sulfate and evaporated down under reduced pressure. The residue was purified by chromatography over a silica gel column (elution with 10:1 dichloromethane/methanol) to give 3.1 g of 1-butoxycarbonylaminocycloprop-1-yl-carbonyl-L-leucyl-glycinamide.

This was treated with 30 ml of an about 6 N solution of hydrogen chloride in dioxane for 15 minutes at room temperature, after which the mixture was evaporated down under reduced pressure and the residue was repeatedly evaporated together with toluene and crystalized from isopropanol/ether. Yield: 2.2 g (60%) of 1-aminocycloprop-1-yl-carbonyl-L-leucyl-glycinamide hydrochloride, mp. =110°–120° C. (isopropanol/ether).

Example 31

D-1,4-Thiazan-3-yl-carbonyl-L-leucyl-glycinamide and L-1,4-thiazan-3-yl-carbonyl-L-leucyl-glycinamide 2.4 g of N-hydroxysuccinimide and 4.2 g of dicyclohexylcarbodiimide were added to 5.6 g of N-benzyloxycarbonyl-D,L-1,4-thiazane-3-carboxylic acid in 40 ml of dioxane at 0°–10° C., 3.8 g of L-leucyl-glycinamide were added after 10 minutes and the mixture was then stirred for 16 hours at room temperature. In the working up procedure, the mixture was taken up in ethyl acetate and the solution was washed successively with 10% strength citric acid solution, sodium carbonate solution and water, dried over sodium sulfate and then evaporated down under reduced pressure. The residue was chromatographed over a silica gel column (elution with 15:1 dichloromethane/methanol) to give 4.6 g of N-benzyloxycarbonyl-D,L-1,4-thiazan-3-yl-carbonyl-L-leucyl-glycinamide.

4.0 g of this derivative were mixed with 50 ml of a 40% strength solution, cooled to 0° C., of hydrogen bromide in glacial acetic acid, and the mixture was stirred for 2 hours at 0° C. It was evaporated down under reduced pressure, the residue was repeatedly evaporated together with toluene, the residue from this was dissolved in water and the solution was brought to pH 9–10 with a strongly basic ion exchanger. The solution was filtered off from the ion exchanger, the filtrate was evaporated down and the residue was chromatographed over a silica gel column (elution with 6:1 dichloromethane/methanol) to give initially 0.9 g (32%) of L-1,4-thiazan-3-yl-carbonyl-L-leucyl-glycinamide, mp. =90°–100° C., $[\alpha]_D^{20} = -22°$ (c =0.5, methanol).

Further elution with the same solvent gave 1.1 g (39%) of D-1,4-thiazan-3-yl-carbonyl-L-leucyl-glycinamide, mp. =152°–157°–C. (isopropanol/ether/hexane), $[\alpha]_D^{20} = -11°$ (c =0.5, methanol).

EXAMPLE 32

Pyrrol-2-yl-carbonyl-L-leucyl-glycinedimethylamide 20 ml of a 40% strength aqueous dimethylamine solution were added to 2.0 g of pyrrol-2-yl-carbonyl-L-leucyl-glycine ethyl ester in 35 ml of methanol and, after 48 hours, the mixture was evaporated down and the residue was chromatographed over a silica gel column (elution with 20:1 dichloromethane/methanol) to give 1.3 g (65%) of pyrrol-2-yl-carbonyl-L-leucyl-glycinedimethylamide, mp. =133°–137° C. (dichloromethane/ether/hexane), $[\alpha]_D^{20} = -13°$ (c =0.5, methanol).

The compounds below were obtained by a method similar to that described in Example 32:

33. Indol-2-yl-carbonyl-L-leucyl-glycinedimethylamide (479%), mp. =150°–155° C. (dichloromethane/ether/hexane), $[\alpha]_D^{20} = +8°$ (c =0.5, methanol).
34. Pyrrol-2-yl-carbonyl-L-leucyl-glycinemethylamide (70%), mp. =95°–108° C. (dichloromethane/ether/hexane), $[\alpha]_D^{20} = +4°$ (c =0.5, methanol).
35. Indol-2-yl-carbonyl-L-leucyl-glycinemethylamide (87%), mp. =108°–114° C. (dichloromethane/ether/hexane), $[\alpha]_D^{20} = +9°$ (c =0.5, methanol).

Examples of pharmaceutical formulations:

EXAMPLE A

The following composition was converted to tablets in a conventional manner on a tablet press:
40 mg of the substance from Example 9
20 mg of corn starch
13.5 mg of gelatine
45 mg of lactose
2.25 mg of Aerosil ® (chemically pure submicroscopic silica)
6.75 mg of potato starch (as a 6% strength paste).

EXAMPLE B

Coated tablets having the following composition were produced in a conventional manner:
20 mg of the substance from Example 9
60 mg of core material
60 mg of sugar-coating material.

The core comprised 9 parts of corn starch, 3 parts of lactose and 1 part of Luviskol ® VA 64 (60:40 vinylpyrrolidone/vinyl acetate copolymer; cf. Pharm. Ind. 1962, 586). The sugar-coating material comprised 5 parts of sucrose, 2 parts of corn starch, 2 parts of calcium carbonate and 1 part of talc. The coated tablets thus obtained were then provided with a shell resistant to gastric juices.

We claim:

1. A compound of the formula I

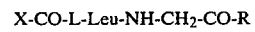
X-CO-L-Leu-NH-CH$_2$-CO-R     I, where X is a saturated or unsaturated 5-membered or 6-membered heterocyclic ring containing not more than 1 heteroatom, said heteroatom consisting of nitrogen but where X cannot be pyrrolidin-2-yl, and R is NH$_2$, and its salts with physiologically tolerated acids.

2. A therapeutic composition for treating depression comprising a pharmaceutically acceptable carrier and from 0.1 to 99% by weight of a compound I as described in claim 1 as the active ingredient.

3. The method of treating depression is a patient suffering therefrom, which comprises adminstering to the patient an antidepressive effective amount of a compound according to claim 1.

4. The method of claim 3, wherein a daily dose of from 0.1 to 100 mg/kg of body weight of the compound is orally administered to the patient.

5. The method of claim 3, wherein a daily dose of from 0.1 to 10 mg/kg of body weight of the compound is parenterally administered to the patient.

6. The compound of claim 1 which is 4,5-Dehydropiperid-2-yl-carbonyl-L-leucyl-glycinamide.

* * * * *